United States Patent [19]

Halpern et al.

[11] 4,036,951
[45] July 19, 1977

[54] ULTRA-VIOLET FILTRATION WITH CERTAIN AMINOSALICYLIC ACID ESTERS

[75] Inventors: Alfred Halpern, Great Neck; Ernest J. Sasmor, Yonkers, both of N.Y.

[73] Assignee: Synergistics, Inc., New York, N.Y.

[21] Appl. No.: 649,891

[22] Filed: Jan. 16, 1976

Related U.S. Application Data

[63] Continuation of Ser. No. 340,481, March 12, 1973, abandoned, which is a continuation-in-part of Ser. No. 145,488, May 20, 1971, abandoned.

[51] Int. Cl.$^2$ .............................................. A61K 7/44
[52] U.S. Cl. ............................. 424/60; 424/DIG. 13; 424/168; 424/362
[58] Field of Search .......................................... 424/60

[56] References Cited

U.S. PATENT DOCUMENTS

| | | | |
|---|---|---|---|
| 2,604,488 | 7/1952 | Freire et al. | 424/60 X |
| 2,647,853 | 8/1953 | Larde et al. | 424/230 |
| 2,667,440 | 1/1954 | Douris et al. | 424/230 |
| 2,676,902 | 4/1954 | Boger et al. | 424/230 |
| 2,853,423 | 9/1958 | La Via | 424/60 |

FOREIGN PATENT DOCUMENTS

| | | | |
|---|---|---|---|
| 700,774 | 12/1953 | United Kingdom | 424/230 |
| 774,107 | 5/1957 | United Kingdom | 424/230 |
| 790,791 | 2/1958 | United Kingdom | 424/230 |

OTHER PUBLICATIONS

J. of American Chemical Soc., 1952, vol. 74, pp. 2589-2593.
Chem. Abs., 1950, vol. 44, pp. 4149h.
Chem. Abs., 1952, vol. 46, pp. 1656e, 2181(b), 4657(b), 9215(b).
Chem. Abs., 1953, pp. 5543(b)and(i).
Chem. Abs., 1954, vol. 48, pp. 9549(c).
Chem. Abs., 1959, vol. 53, pp. 6533(g).
Chem. Abs., 1959, vol. 53, pp. 2057(c).
Chem. Abs., 1962, vol. 56, pp. 8843(g).
Chem. Abs., 1965, pp. 18912(c).

*Primary Examiner*—Dale R. Ore
*Attorney, Agent, or Firm*—Wolder & Gross

[57] ABSTRACT

Alkyl esters of aminosalicylic acid, said alkyl group having from 1 to 18 carbon atoms in chain length; alkenyl esters of aminosalicylic acid, said alkenyl group selected from the group consisting of vinyl, allyl, undecenyl, oleyl and linolenyl groups, and cyclic esters of aminosalicylic acid, said cyclic group being the cyclohexyl, phenyl and menthyl groups, having ultra-violet screening properties to absorb light rays within the wave-length range of 2950 A. to 3200 A. while transmitting the light rays beyond the 3200 A. range to permit the desirable tanning of the skin without solar burn. The respective esters of aminosalicylic acid are prepared by the reduction of the appropriate nitro-salicylic acid ester with Raney nickel and hydrogen in the presence of ethyl acetate. The respective esters are obtained as oils or solid crystalline substances and are soluble in alcohols, chloroform, acetone and benzene but insoluble in water. The ultra-violet absorption spectra for the respective compounds are described. Compositions comprising the above compounds together with the method for their preparation and the method for the use to achieve an ultraviolet filtering action on the skin of humans and animals are described.

14 Claims, No Drawings

ULTRA-VIOLET FILTRATION WITH CERTAIN AMINOSALICYLIC ACID ESTERS

This application is a continuation of application Ser. No. 340,481, filed Mar. 12, 1973, now abandoned, which in turn was a continuation-in-part of application Ser. No. 145,488, filed May 20, 1971, now abandoned.

This invention relates to a method for the use of certain aminosalicylic acid derivatives and compositions containing the same to achieve a sunburn preventative action. In particular it is concerned with the ultra-violet screening activity of alkyl esters of aminosalicyclic acid, said alkyl group being from 1 to 18 carbon atoms in chain length; alkenyl esters of aminosalicylic acid, said alkenyl group selected from the group consisting of vinyl, allyl, undecenyl, oleyl and linolenyl groups, and cyclic esters of aminosalicyclic acid, said cyclic group being hexyl, phenyl and menthyl groups as ultra-violet screening agents. It is also intended to describe pharmaceutical compositions such as wax-sticks, ointments, lotions and solutions containing the aforesaid compounds and the use of said pharmaceutical compounds in achieving a tanning action on the skin of humans and animals, but without accompanying solar burn.

It is well known that rays within the ultra-violet spectrum, having a wave-length of from 2950 to 3850 Angstrom units, will result in a hyperpigmentation or tanning of human or animal skin through a stimulation of the cells capable of producing melanin. Within this portion of the light spectrum it has further been determined that the wave-length of between 2950 A°. to 3150 A°. are particularly potent in causing an erythematous skin reaction and this range in wave-length of light is generally referred to as the "burn range." However, the light rays within the range of from 3300 A°. to 3850 A°. are capable of causing a desirable stimulation of the tissue melanin-producing system to result in direct tanning of skin without accompanying erythema or burn. Thus it has become accepted that a satisfactory sun screen compound must effectively block ultra-violet light within the wave-length range of 2950 A°. to 3150 A°. while transmitting the light rays beyond the 3150 A°. wave-length. Preferably, the filtering capacity of the ultra-violet screening agent should be between 3460 A°. and 3650 A°. so that tanning of the skin will be accomplished without the occurrence of erythema and consequent pain and suffering accompanying solar burn.

To achieve this goal, literally hundreds of compounds have been proposed as sun screen agents, each described as capable of absorbing ultra-violet light within the "burn range" but transmitting the physiologically desirable and cosmetically preferred tanning rays. For example, such agents as salicylate compounds, to include, benzyl salicylate, methyl salicylate, glyceryl mono salicylate; benzoic acid derivatives, to include ethyl, propyl and butyl esters of para-amino benzoic acid and even para-amino benzoic acid itself; pyrimidines, sulfonic acid compounds, natural products, such as umbilliferone and a whole host of diverse synthetic chemical agents each designed to produce a particular type screening effect within the tanning range of light. Virtually all of the compounds suggested have some limitation to restrict their use. For example, the class of salicylic acid derivatives as sun screen compounds are water-soluble derivatives which are readily removed by water. The insoluble salicylate compounds dry to an undesirable solid on the skin to form a porous, cracked film to reduce the effectiveness of the preparation as a sun screen. The benzoic acid esters exert a local anaesthetic effect as well as being strong sensitizing agents thereby being considered physiologically undesirable. The more complex organic compounds, while effective for special purposes, have objectionable odors and may induce a photo-sensitivity which is generally not reversible. Moreover, it is well known that many of the sun-screen agents are capable of causing allergic reactions requiring that the subject stop their use and seek another compound or else suffer acute distress and disability of solar burn. It is for these reasons that the search for new and effective sun screen compounds continues and is of necessity despite the myriad of compounds discovered and alleged to have these properties.

It was unexpectedly found that certain alkyl esters of aminosalicylic acid, said alkyl group being from 1 to 18 carbon atoms is chain length; alkenly esters of aminosalicylic acid, said alkenyl group selected from the group consisting of vinyl, allyl, undecenyl, oleyl and linolenyl groups, and, cyclic esters of aminosalicylic acid, said cyclic group being selected from the group consisting of cyclohexyl, phenyl and menthyl groups, have beneficial ultra-violet screening properties to absorb light rays over the wave-length of 2950 A°. to 3150 A°., while transmitting rays over the wave-length beyond the 3200 A°. range, thereby permitting a desirable tanning of the skin without solar burn. Moreover, the optimal absorption range of the aforesaid amino salicylic acid esters in such as to permit a maximal transmission over the wave-length between 3460 A°. and 3800 A°., thus preferably filtering the ultra-violet light to remove the burning rays.

p-Aminosalicylic acid is a well known compound having a wide therapeutic use as a tuberculostatic agent and is capable of forming metallic salts and esters which are similarly employed in turberculoses therapy. The phenyl ester of para-aminosalicylic acid is described in U.S. Pat. No. 2,604,488 (issued July 22, 1952).

The esters of aminosalicylic acid may be prepared by the reduction of the corresponding nitrosalicylic acid ester, dissolved in ethyl acetate, using Raney nickel as a catalyst and hydrogen under pressure. The resultant yield of the respective aminosalicylic acid ester is excellent and the respective compounds are obtained as oils or white crystalline substances and may be purified by distillation under reduced pressure or crystallization. The respective esters of aminosalicylic acid are insoluble in water but soluble in alcohols, acetone, benzene, chloroform and vegetable oils.

When an alkyl or alkenyl ester of aminosalicylic acid is desired, then these may be prepared from either the alkyl-ortho-meta or para-nitrosalicylate, said alkyl or alkenyl group may range from 1 to 18 carbon atoms in chain length. The resultant alkyl aminosalicylate, wherein said alkyl group has from 1 to 18 carbon atoms in chain length may be purified by distillation in vacuum (below 2 mm. Hg. pressure) or by crystallization.

Those esters wherein the alkyl or alkenyl group is between 1 to 6 carbon atoms in chain length are oily or waxy in character and distill over the temperature range of below 180° C at 2 mm. Hg. Those esters in which said alkyl group is from 6 to 18 carbon atoms in chain length are obtained as solids, crystallized from alcohol-water solution. The solid aminosalicylate esters are white crystalline or waxy substances, insoluble in water but soluble in the usual fatty solvents and alcohol.

The alkyl and alkenyl aminosalicylic acid ester compounds described above were found to possess unique ultra-violet screening properties by the well known spectroscopic method for determining the ultra-violet absorbing capacity of the compound. A standard reference to this method is "Organic Chemistry" by H. Gilman, Volume III, p. 127, et. seq., John Wiley and Sons, New York, (1953). In the evaluation of the ultra-violet absorption capacity of the compounds, the wave-length of the band of the maximum absorption is the important factor in determining whether a compound is suitable as an ultraviolet screening substance. A useful means of expressing the degree of light absorption is the absorption co-efficient. The ultra-violet absorption selections are determined spectrophotometetrically utilizing the conventional ultraviolet spectrometer and an appropriate solution of the compound to be tested. The absorption co-efficient at the wave-length of maximum absorption designated as a max is an expression of the wave-length of maximum absorption and is calculated from the following formula relationship:

$$a = -\frac{1}{bc} \log \frac{T}{To}$$

wherein
$a$ is the absorption co-efficient
$b$ is the thickness of the spectrophotometric cell in centimeters
$c$ is the concentration in grams per liter
$T$ is the amount of light passing through solution
$To$ is the amount of light passing through the solvent only in the same cell.

When this test was applied to the aforesaid compounds, it was found that the ultra-violet rays of the wave-length from 2950 A°. to 3200 A°., which have been shown to cause solar burning, evidenced by erythema, pain and skin edema, were effectively absorbed or blocked, while those ultra-violet light rays within the wave-length of between 3300 A°. and 3800 A°. (established cause a desirable and beneficial tanning of the skin) were permitted to pass. Moreover, a preferred range of ultra-violet filtration occured between the wave-length of 3460 A°and 3800 A°., thereby selectively filtering the tanning rays from the solar burning rays in the ultra-violet spectrum. It was found that the aforesaid new compounds had an absorbance range of between 0.6 and 1 for the noxious ultra-violet burning rays within the wave-length of from 2850 A°. to 3150 A°., whereas there was virtually no absorbance of the ultra-violet rays in the wave-length between 3460 A°. to 3800 A°.

Compositions comprising the sun screen compounds described above, may be prepared in the form of solutions, lotions, creams, ointments, wax-sticks. Solutions may be packaged as an aerosol spray for convenience of application. Whatever the dosage form selected, the concentration of the respective sun screen substance is from 0.5 percent to 25 percent by weight. The compositions will be found to be stable and possess certain unique, advantageous and desirable properties in preventing sunburn and causing a tanning of the skin in humans and animals.

When it is desired to effectively screen the ultra-violet light to achieve a tanning action without solar burning, then the aforesaid preparations are applied to the skin prior to exposure to ultra-violet light in a therapeutically sufficient quantity to provide a uniform coating.

Both water-soluble and water-insoluble carriers may be employed, depending upon the individual preference.

While it is known that the free acid, para-amino salicylic acid and its metal salts cause skin irritation and dermal eruptions, such allergic and skin irritant actions are notably absent for the above described alkyl and alkenyl aminosalicylic acid esters and the new compounds are singularly free from any of the aforesaid noxious skin reactions associated with p-aminosalicylic acid and its metal salts. It was further found that when the above described compounds and compositions containing the same, were applied to sunburned skin or skin exposed to an excess amount of ultra-violet irradiation, that a soothing, calmative effect occurred with a consequent rapid disappearance of local pain, tenderness and sensitivity. Thus the action of the aforesaid respective active compounds and compositions containing the sane is extended beyond the ultra-violet screening effect to one of causing a healing action on sunburned skin as well as the skin exhibiting the effects of excess ultra-violet radiation. The mechanism for this unexpected desirable dermal effect may be postulated to occur by a topical analgesic and anaesthetic action. When it is desired to counteract the erythema, pain, tenderness and other local topical dermal reactions to sunburn or excess ultra-violet irradiation, then the aforesaid active compounds and compositions containing the same, are applied to the affected skin site from 1 to 6 times daily. An immediate cooling, soothing local response will be observed and pain and tenderness will be promptly eliminated. The erythema will blanche within a reasonable period of time and be replaced by conventional tanning.

The following examples illustrate the scope of the present invention but it is not intended to limit the invention thereby.

EXAMPLE 1

In a suitable vessel containing 1 gm. mol of meta-aminosalicylic acid is added 1 gm. mol of phenol and 0.5 mol of tetraphosphoric acid. The mixture is stirred and auto-claved for one hour after which time it is poured into water. The solid material is filtered, suspended in acetone and neutralized with sodium hydroxide to pH 6. Dilute ammonia solution is added to prepicitate phenyl-p-aminosalicylate which is separated by filtration and dried. The white crystalline powder is phenyl-m-aminosalicylate, melting between 158° C and 163° C.

In place of the meta-aminosalicylic acid described above, there may be substituted an equimolar quantity of ortho-aminosalicylic acid. The remainder of the steps being the same and the resultant compound is the respective phenyl-ortho-aminosalicylate.

EXAMPLE 2

One-tenth mol of methyl-m-nitrosalicylate is dissolved in 250 ml. of ethyl acetate and 10 gms. of Raney nickel added. The mixture is placed in a suitable container to permit pressure hydrogenation and hydrogen gas is passed into the solution. When the gas pressure reaches 10 pounds psi. at 80° C., the mixture is agitated and when the absorption of hydrogen has reached equilibrium, it is shaken for four hours and cooled. The mixture is filtered and the formed methyl-m-aminosalicylat is isolated by distillation and is obtained as an oily compound which distills at 126° C. at 2 mm. Hg. pressure.

EXAMPLE 3

In place of the methyl-m-nitrosalicylate of Example 2 there may be substituted in equimolar portions, an appropriate alkyl-nitrosalicylate ester selected from the group consisting of alkyl-ortho-nitrosalicylate compounds wherein said alkyl group is from 1 to 18 carbon atoms in chain length, alkyl-meta-nitrosalicylate compounds, wherein said alkyl group is from 2 to 18 carbon atoms in chain length and alkyl-p-nitrosalicylate wherein said alkyl group is from 1 to 18 carbon atoms in chain length. The remainder of the steps are the same and the respective ortho, meta or para-aminosalicylate alkyl ester is obtained.

EXAMPLE 4

One-tenth mol of an alkali metal salt of para-aminosalicylic acid as for example, sodium-p-aminosalicylate, potassium-p-aminosalicylate or lithium-p-aminosalicylate, is dissolved in 300 ml. of alcohol and to this is added exactly one-tenth mol of a menthyl halogen salt as for example, methyl chloride, menthyl bromide or menthyl iodide. The mixture is stirred and 0.5 gms. of freshly precipitated silver hydroxide is added as a catalyst. The mixture is warmed to 50° C. for a period of at least two hours, cooled to room temperature and filtered. The filtrate is set aside to crystallize in an ice-chest and menthyl-para-aminosalicylate is obtained as a white crystalline substance melting at 187° C. to 189° C. The compound is insoluble in water but soluble in alcohol, benzene and chloroform.

In place of the alkali metal-para-aminosalicylate salt described above, there may be substituted in equivalent molar quantities, an alkali metal-ortho-aminosalicylate or an alkali metal-meta-aminosalicylate. The remainder of the steps being the same and the formed compound obtained is the respective menthyl-ortho-aminosalicylate (mp. 201° C. -206° C.) or menthylmeta-aminosalicylate (mp. 173° C. -178° C).

EXAMPLE 5

In place of the menthyl chloride described in Example 4, there may be substituted equimolar quantities of cyclohexyl chloride, cyclohexyl bromide or cyclohexyl iodide. The remainder of the steps being the same and the resultant compound formed is the respective cyclohexyl-para-aminosalicylate, cyclohexyl meta-aminosalicylate and cyclohexyl ortha-aminosalicylate.

EXAMPLE 6

The ultra-violet filtering capacity of the respective compounds obtained from Examples 1 through 5 above, was determined with the Beckman Spectrometer, in the following manner:

One-hundred mg. of the slected compound was dissolved in 100 ml. of ethanol and 10 ml. of this solution was diluted with water to make 1 liter. The concentration of active compound in the diluted solution is 0.001 percent, by weight. A one-centimeter spectrophotometric cell is filled with the diluted solution of the selected active-compound containing 0.001 percent by weight of active compound and the ultra-violet spectrum of the solution is determined. A solvent control or blank solution is prepared by dissolving 10 ml. of ethanol in 1 liter of distilled water and the ultra-violet spectrum determined in the same manner for the blank or solvent control solution. The absorption co-efficient for the respective compound is calculated from the formula:

$$a = -\frac{1}{bc} \log \frac{T}{To}$$

wherein $a$ is the absorption co-efficient $b$ is the thickness of the spectrophotometric cell in centimeters $c$ is the concentration in grams per liter $T$ is the amount of light passing through solution $To$ is the amount of light passing through the solvent only in the same cell.

It will be seen that the greater the absorbance value for a particular wave-length, the less light is transmitted. Thus, a high absorbance value for the wave-length range of from 2950 A°. to 3150 A°., the less will be the tendency for solar burning, whereas the converse effect is desired for the beneficial tanning wave-length range of from 3460 A°. to 3800 A°., and in particular the range of 3460 A°. and 3650 A°., wherein a low absorbance is desired. The ultra-violet absorption capacity of the respective formed compounds was found to be as follows:

TABLE 1

| | Filtering Capacity of Certain Aminosalicylic Acid Esters | |
|---|---|---|
| Compound (0.001 % conc.) | Absorbance Wave-length range 2950 Å.-3150 Å. | Absorbance of Wave-length range 3460 Å.-3650 Å. |
| methyl-p-aminosalicylate | 0.80 – 0.93 | nil |
| ethyl-p-aminosalicylate | 0.81 – 0.93 | nil |
| propyl-p-aminosalicylate | 0.81 – 0.91 | nil |
| isopropyl-p-aminosalicylate | 0.82 – 0.92 | nil |
| butyl-p-aminosalicylate | 0.86 – 0.94 | nil |
| isobutyl-p-aminosalicylate | 0.85 – 0.91 | nil |
| amyl-p-aminosalicylate | 0.87 – 0.97 | nil |
| hexyl-p-aminosalicylate | 0.83 – 0.92 | nil |
| septyl-p-aminosalicylate | 0.81 – 0.89 | nil |
| octyl-p-aminosalicylate | 0.82 – 0.95 | nil |
| nonyl-p-aminosalicylate | 0.87 – 1.00 | nil |
| decyl-p-aminosalicylate | 0.82 – 0.93 | nil |
| lauryl-p-aminosalicylate | 0.87 – 1.00 | nil |
| myristyl-p-aminosalicylate | 0.81 – 0.97 | nil |
| cetyl-p-aminosalicylate | 0.82 – 0.98 | nil |
| stearyl-p-aminosalicylate | 0.82 – 0.97 | nil |
| phenyl-p-aminosalicylate | 0.95 – 1.00 | nil |
| cyclohexyl-p-aminosalicylate | 0.93 – 1.00 | nil |
| menthyl-p-aminosalicylate | 0.98 – 1.00 | nil |
| methyl-m-aminosalicylate | 0.81 – 0.92 | nil |
| ethyl-m-aminosalicylate | 0.78 – 0.91 | nil |
| propyl-m-aminosalicylate | 0.79 – 0.89 | nil |
| isopropyl-m-aminosalicylate | 0.84 – 0.91 | nil |
| butyl-m-aminosalicylate | 0.86 – 0.95 | nil |

TABLE 1-continued

Filtering Capacity of Certain Aminosalicylic Acid Esters

| Compound (0.001 % conc.) | Absorbance Wave-length range 2950 Å.–3150 Å. | Absorbance of Wave-length range 3460 Å.–3650 Å. |
|---|---|---|
| isobutyl-m-aminosalicylate | 0.83 – 0.92 | nil |
| amyl-m-aminosalicylate | 0.88 – 0.98 | nil |
| hexyl-m-aminosalicylate | 0.80 – 0.96 | nil |
| septyl-m-aminosalicylate | 0.83 – 0.94 | nil |
| octyl-m-aminosalicylate | 0.87 – 0.96 | nil |
| nonyl-m-aminosalicylate | 0.86 – 0.97 | nil |
| decyl-m-aminosalicylate | 0.85 – 0.94 | nil |
| lauryl-m-aminosalicylate | 0.85 – 0.95 | nil |
| myristyl-m-aminosalicylate | 0.87 – 0.97 | nil |
| cetyl-m-aminosalicylate | 0.83 – 0.92 | nil |
| stearyl-m-aminosalicylate | 0.84 – 0.94 | nil |
| phenyl-m-aminosalicylate | 0.92 – 0.99 | nil |
| cyclohexyl-m-aminosalicylate | 0.87 – 0.91 | nil |
| menthyl-m-aminosalicylate | 0.96 – 1.00 | nil |
| methyl-o-aminosalicylate | 0.83 – 0.91 | nil |
| ethyl-o-aminosalicylate | 0.81 – 0.89 | nil |
| propyl-o-aminosalicylate | 0.84 – 0.92 | nil |
| ispropyl-o-aminosalicylate | 0.83 – 0.91 | nil |
| butyl-o-aminosalicylate | 0.84 – 0.92 | nil |
| isobutyl-o-aminosalicylate | 0.86 – 0.94 | nil |
| amyl-o-aminosalicylate | 0.84 – 0.91 | nil |
| hexyl-o-aminosalicylate | 0.83 – 0.93 | nil |
| septyl-o-aminosalicylate | 0.81 – 0.91 | nil |
| octyl-o-aminosalicylate | 0.80 – 0.94 | nil |
| nonyl-o-aminosalicylate | 0.84 – 0.96 | nil |
| decyl-o-aminosalicylate | 0.87 – 0.97 | nil |
| lauryl-o-aminosalicylate | 0.83 – 0.92 | nil |
| myristyl-o-aminosalicylate | 0.85 – 0.94 | nil |
| cetyl-o-aminosalicylate | 0.83 – 0.95 | nil |
| stearyl-o-aminosalicylate | 0.84 – 0.96 | nil |
| phenyl-o-aminosalicylate | 0.93 – 1.00 | nil |
| cyclohexyl-o-aminosalicylate | 0.92 – 0.98 | nil |
| menthyl-o-aminosalicylate | 1.00 – 1.00 | nil |

It will be observed that the respective compounds possess a high absorbance value within the solar burning wave-length of ultra-violet light ranging from 2950 A°. to 3150 A°., while permitting the beneficial tanning rays to pass virtually unaffected. The range in absorption of the harmful solar burning ultra-violet rays was between 0.6 and 0.9 for aminosalicylic acid and its salts, and a more complete filtering occurred with the absorbance approaching 1., for the aminosalicylate esters. The compounds exhibited virtually no interruption of the beneficial tanning rays over the wave-length between 3400 A°. and 3300 A°. These absorbance values establish the new compounds to be effective ultra-violet screen agents.

EXAMPLE 7

To a solution of 0.5 gm. mol of alkali metal para-aminosalicylate salt, as for example the respective sodium, potassium or lithium salts dissolved in 500 ml. of ethanol is added 0.5 gm. mol of undecenyl chloride. The mixture is stirred and warmed to about 60° C. for at least four hours. The separated sodium chloride is filtered and the alcohol solution set aside to crystallize. A white waxy solid is obtained which melts between 80° C. and 85° C. and is undecenyl para-aminosalicylate.

In a similar manner, equimolar concentrations of vinyl chloride, allyl chloride, oleyl chloride, linolenyl chloride, vinyl bromide, allyl bromide, undecenyl bromide, oleyl bromide, linolenyl bromide, vinyl iodide, allyl iodide, undecenyl iodide, oleyl iodine or linolenyl iodide may be used in place of the undecenyl chloride described above and the respective formed alkelyl p-aminosalicylate ester is obtained.

In place of the metal-para-aminosalicylate salt described above there may be substituted in equimolar proportions a metal-meta-aminosalicylate salt or a metal-ortho-aminosalicylate salt, said metal being sodium, potassium or lithium or ammonium. The remainder of the steps being the same and the respective formed alkenyl meta-aminosalicylate ester and alkanyl ortho-aminosalicylate ester described above is obtained.

When the ultra-violet absorbance is determined for the above alkenyl esters, the following values are obtained:

TABLE 2

| Compound (0.001% conc.) | Absorbance at the Wave-length range 2950 Å.–3150 Å. | Absorbance at the Wave-length range 3460 Å.–3650 Å. |
|---|---|---|
| vinyl-p-aminosalicylate | 0.94 – 1.00 | nil |
| allyl-p-aminosalicylate | 0.95 – 1.00 | nil |
| undecenyl-p-aminosalicylate | 0.95 – 1.00 | nil |
| oleyl-p-aminosalicylate | 0.97 – 1.00 | nil |
| lineolenyl-p-ainosalicylate | 0.97 – 1.00 | nil |
| vinyl-m-aminosalicylate | 0.92 – 1.00 | nil |
| allyl-m-aminosalicylate | 0.91 – 1.00 | nil |
| undecenyl-m-aminosalicylate | 0.95 – 1.00 | nil |
| oleyl-m-aminosalicylate | 0.95 – 1.00 | nil |
| linolenyl-m-aminosalicylate | 0.96 – 1.00 | nil |
| vinyl-o-aminosalicylate | 0.92 – 1.00 | nil |
| allyl-o-aminosalicylate | 0.93 – 1.00 | nil |
| undecenyl-o-aminosalicylate | 0.93 – 1.00 | nil |
| oleyl-o-aminosalicylate | 0.95 – 1.00 | nil |
| linolenyl-o-aminosalicylate | 0.96 – 1.00 | nil |

EXAMPLE 8

When it is desired to utilize a solution of the appropriate sun screen compound described in Examples 1 to 7 above, then either an aqueous, alcoholic or oil solution may be used. Aqueous solutions are prepared with water-soluble metallic salts of aminosalicylic acid as for example, the respective sodium, potassium, lithium, and ammonium amonisalicylic acid salts. The appropriate quantity of the selected compound is dissolved in 90 percent of the final desired volume of water with a concentration of active sun screen compound of from 0.5 percent to 25 percent by weight with a preferred concentration of from 3 percent to 10 percent by weight of sun screen compound. The solution may be clarified by treating with charcoal and filtering. It may be desired to adjust the pH to between pH 6 and pH 8. This may be readily accomplished through the use of sodium acid phosphate or other suitable buffer agent. The solution is then brought to final volume and packaged into dosage form of suitable size and shape.

Alcoholic solutions are prepared in a similar manner and such alcohols as ethanol, and isopropanol are preferred as the solvent. It may be found desirable to dilute the alcohol solvent with water thus forming a hydroalcoholic solution, in which case the concentration of water may range from equal parts of water and alcohol to 10 parts of water and 90 parts of alcohol.

Oil solutions may be prepared by dissolving the appropriate alkyl, alkenyl or cyclic ester of ortho-aminosalicylic acid, meta-aminosalicylic acid and para-aminosalicylic acid as described above or to utilize ortho, meta or para-aminosalicylic acid. The range in concentration of either the selected aminosalicylic acid ester or the aminosalicylic acid as described above is from 0.5 percent to 25 percent by weight, with a preferred concentration of from 3 percent to 10 percent by weight of sun screen compound.

To prepare an oil sun creen solution, then the appropriate quantity of the selected cyclic, alkyl or alkenyl ester of aminosalicylic acid described above is dissolved in a suitable oily vehicle, as for example, cottonseed oil, poppy-seed oil, peanut oil, corn oil and liquid petrolatum. Suitable anti-oxidants and other fat preservatives as well as perfume agents may be added and the oil solution is brought to proper volume. The finished oil sun screen solution is filtered and packaged in unit containers of suitable size and shape.

EXAMPLE 9

When it is desirable to prepare an ointment, then either an oleagenous carrier as for example, petrolatum and hydrophylic or lipophylic emulsion ointment bases and water-soluble ointment bases may be used as vehicles. Such ointment preparations contain from 0.5 percent to 25 percent by weight of the respective active sun screen compound described above with a preferred range in concentration of active sun screen compound of between 3 percent and 10 percent by weight. Typical ointments of the types set forth above may be prepared as follows:

| (a) | Cleagenous Ointments | |
|---|---|---|
| | Phenyl para-aminosalicylate | 10 grams |
| | Petrolatum U.S.P. q.s. | 100 grams |

Melt approximately 80 grams of the petrolatum, using care not to overheat. The phenyl para-aminosalicylate is added and stirred until dissolved, after which time the mixture is brought to final weight and allowed to cool to room temperature. The preparation may be packaged either in the molten state or in the solidified form, in unit containers of suitable size and shape. Should it be preferred to add perfume agents then these are added just prior to the solidification of the molten mass.

| (b) | Water-in-Oil Emulsion Base | |
|---|---|---|
| | Menthyl para-aminosalicylate | 3 grams |
| | Cholesterol | 3 grams |
| | Stearyl alcohol | 3 grams |
| | White wax | 8 grams |
| | White petrolatum, q.s. | 100 grams |

Melt the stearyl alcohol, white wax and about 70 grams of the white petrolatum, on a steam bath. Add the cholesterol and stir until all have dissolved. In a separate container melt about 3 grams of white petrolatum and to this add the menthyl para-aminosalicylate, stir until dissolved and add to the mixture of stearyl alcohol, white wax and petrolatum. Mix well and bring to proper weight (100 grams) with additional molten white petrolatum, remove from the heat and stir until congealed.

The resultant sun screen ointment may be utilized in the anhydrous form or mixed with water to form a water-in-oil emulsion base. If it is desired to prepare the water-in-oil base, then the appropriate amount of water is added before the mixture congeals and the hydrated ointment homogenized. The amount of water to be included in such preparations will vary with the desired degree of hardness. A preferred range of hydration for such water-in-oil emulsion bases is from 10 percent to 30 percent by weight of water.

| (c) | Water-in-Oil Emulsion Base | |
|---|---|---|
| | Ethyl meta-aminosalicylate | 35 grams |
| | Cetyl alcohol | 15 grams |
| | White wax | 1.5 grams |
| | Propylene glycol | 10 grams |
| | Sodium lauryl sulfate | 2 grams |
| | Water, q.s. | 100 grams |

Melt the cetyl alcohol and white wax with half the weight of proplyene glycol, avoiding heating above 60° C. To the remainder of the propylene glycol add the ethyl-meta-amino salicylate and stir until a homogenous mixture is obtained. The propylene glycol solution of the selected sun screen compound is added to the molten cetyl alcohol-white wax mixture and stirred well. Dissolve the sodium lauryl sulfate in about 45 grams of water with the aid of heat, avoiding temperature above 60° C. Slowly add the oil phase to the water phase, with rapid stirring while maintaining the heat. After about five minutes of rapid stirring, bring to proper weight with additional warm water and stir until congealed. The oil-in-water emulsion sun screen ointment is then milled or homogenized and packaged into suitable unit containers.

A sun screen vanishing cream may also be prepared by mixing the selected active compound with a pharmaceutically acceptable vanishing cream carrier. Thus 0.5 percent by weight of cyclohexyl-ortho-aminosalicylate is added to a sufficient quantity of cold cream and the mixture levigated until a uniform preparation results.

| (d) Water-soluble Ointment Bases | |
|---|---|
| A typical water-soluble sun screen ointment is as follows: | |
| Selected aminosalicylate sun screen agent | 100 grams |
| Polyethylene glycol-400 | 500 grams |
| Polyethylene glycol-4000 | 600 grams |

Heat the two glycol ingredients (on a water bath) to about 60° C. remove from the heat and stir. Add the selected active compound to the base before it hardens and stir to obtain a uniform mixture. A firmer ointment preparation may be made by replacing a portion of the polyethylene glycol-400 with polyethylene glycol-4000. Between 5 percent and 25 percent of water may be incorporated into the base, in which event approximately 10 percent of the weight of polyethylene glycol-4000 utilized is replaced with an equal weight of stearyl alcohol.

It may be found desirable to utilize other polyethyelene glycol compounds in preparing the base, as for example a polyethylene glycol compound having a molecular weight of between 200 and 800, in place of the polyethylene glycol-400 and a polyethylene glycol compound having a molecular weight of between 1,000 and 6,000 in place of the polyethylene glycol-4000. Such modification of the formula will result in different degrees of ointment firmness for the finished preparation but will influence only its cosmetic properties and not its sun screen capacity.

In place of any of the active sun screen agents used as described above there may be substituted any of the compounds described above in a concentration of selected active sun screen compound ranging from 0.5 percent to 25 percent by weight. Appropriate adjustment in the amount of ointment base is made for the increased or decreased concentration of active compound. The ointment base formulations described above are only intended to illustrate the class of ointment compositons pharmaceutically acceptable to prepare the new sun screen preparations and other ointment bases of the oleagenous type, water-in-oil emulsion bases, oil-in-water emulsion bases and water-soluble ointment bases may be used interchangeably without affecting the sun screen properties of the resultant composition.

EXAMPLE 10

Lotions are liquid suspensions or dispersions intended for external application to the body and are prepared by triturating the ingredients to a smooth paste with a portion of the liquid phase and then adding the remainder of the liquid. High speed mixers and homogenizers are used to obtain a uniform dispersion. An example of sun screen lotions comprising the aforesaid active sun screen compound described above and a lotion-vehicle, is as follows:

| Phenyl-para-aminosalicylate | 5 grams |
|---|---|
| Glycerin | 2 ml. |
| Hydrated microcrystalline cellulose | 2 grams |
| Carboxy methyl cellulose | 2 grams |
| Rose-water q.s. | 100 grams |

The phenyl-aminosalicylate is mixed with glycerin, hydrated microcrystalline cellulose and about 20 ml. of rose-water to prepare a smooth paste. The carboxy metal cellulose is separately added to 20 ml. of rose-water and warmed until uniform dispersion results and the whole is added to the paste prepared earlier. The mixture is stirred rapidly while adding sufficient rose-water to bring to final volume.

In place of the glycerin described above there may be substituted any aqueous vehicle as for example, distilled water, a hydroalcoholic solution containing from 60 to 80 parts of water and 20 to 40 parts of alcohol, pharmaceutically acceptable aromatic water or mixtures of these.

In place of the glycerin described above there may be added propylene glycol and/or a liquid polyethylene glycol having a molecular weight of from 200 to 800 in either the same concentration or in varying concentration of between 1 percent and 5 percent, by weight.

EXAMPLE 11

Should it be desired to prepare a wax-stick sun screen preparation then this may be prepared by combining the selected sun screen compound as described in Examples 1 through 7 above in concentration of from 0.5 percent to 25 percent by weight with a preferred concentration of 3 percent to 10 percent by weight in a suitable wax-base which is then shaped into a rod and cut into desired size. A suitable base for this purpose is as follows:

| White-wax | 3 parts |
|---|---|
| Spermaceti | 3 parts |
| Cetyl alcohol | 3 parts |
| White petrolatum | 5 parts |

Melt the ingredients on a water-bath while stirring, and remove from heat. The appropriate quantity of the selected sun screen agent described above is then incorporated into the molten mixture and stirred and the whole poured into a suitable mold and allowed to congeal into sticks of proper size and shape.

Such sun screen wax-sticks are useful to protect the lips and the eyelids against solar burning. It has the particular advantage of permitting spot application to an area without spreading.

EXAMPLE 12

When it is desired to block the noxious solar burning rays or to prevent ultra-violet burning, then any of the compounds described above or compositons containing the same, is applied to the skin surface of a human or an animal prior to exposure of the skin surface to either sunlight or ultra-violet light. The ultra-violet screen is applied in sufficient quantity to provide continuous skin surface film of at least 0.1 mm, thick with a preferred thickness of said surface film being between 0.3mm. and 0.5mm. The presence of the skin surface film containing the new sun screen filtering compound will effectively protect the treated area against solar burning while permitting the beneficial and desirable tanning ultra-violet rays to pass through. The frequency of application of the sun screen protective composition will depend upon its removal from the external surface, by bathing or other means, and the preparation may be reapplied whenever required.

After exposure of the skin of humans or animals which previously treated with the above described sun screen compounds or pharmaceutical compositions containing the same to ultra-violet light or solar irradiation a rapid tanning effect will be observed without intervening solar burning and its consequent distress and injury. The above described sun screen compounds and the pharmaceutical compositions containing the same are non-irritating and non-sensitizing to human and animal skin and will not cause skin eruptions.

EXAMPLE 13

When it is desired to soothe or allay the pain and distress accompanying sunburn then suitable pharmaceutical compositons containing any of the active ingredients described above may be applied to the affected surface from 1 to 4 times daily. Although the pharmaceutical compositions described above exert an equal beneficial effect to a sunburned area, ointments are a preferred dosage form to cover the larger areas of body surface while the aqueous lotion is preferred to treat a blistered area. After appropriate application of the above described compositions to the affected skin surface area of humans or animals, a prompt, soothing action results with relief of pain, tenderness and local distress. The skin edema of the solar burn is reduced and the erythema will blanche to be replaced by a desired beneficial tanning.

What is claimed is:

1. The method of preventing solar burning in a human or animal comprising applying to the skin of said human or animal a composition containing 0.5 to 25 percent by weight of a compound selected from the group consisting of phenylorthoaminosalicylate, phenylmeta-aminosalicylate, phenyl-para-aminosalicylate and methyl-para-aminosalicylate and a carrier pharmaceutically acceptable for topical application prior to exposing said skin to solar radiation.

2. The method of claim 1 wherein said sun-screen compound is phenyl-para-aminosalicylate.

3. The method of claim 1 wherein said sun-screen compound is menthyl-para-aminosalicylate.

4. The method of claim 1 wherein said carrier is a lotion vehicle.

5. The method of claim 1 wherein said carrier is an ointment base carrier.

6. The method of claim 1 wherein said carrier is a solid wax-stick carrier.

7. The method of claim 1 wherein said carrier is a solution selected from the group consisting of aqueous, alcoholic and oil solutions.

8. The method of treating an ultra-violet radiation dermal burn, comprising applying to said ultra-violet burned area one to six times daily a composition containing 0.5 to 25 percent by weight of a compound selected from the group consisting of phenylorthoaminosalicylate, phenylmeta-aminosalicylate, phenyl-para-aminosalicylate and menthyl-para-aminosalicylate and a carrier pharmaceutically acceptable for topical application.

9. The method of claim 8 wherein said sun-screen compound is phenyl-para-aminosalicylate.

10. The method of claim 8 wherein said sun-screen compound is menthyl-para-aminosalicylate.

11. The method of claim 8 wherein said carrier is a lotion vehicle.

12. The method of claim 8 wherein said carrier is an ointment base carrier.

13. The method of claim 8 wherein said carrier is a solid wax-stick carrier.

14. The method of claim 8 wherein said carrier is a solution selected from the group consisting of aqueous, alcoholic and oil solutions.

* * * * *